(12) United States Patent
Lacayo

(10) Patent No.: US 9,440,041 B1
(45) Date of Patent: Sep. 13, 2016

(54) MEDICINAL HEALING BOOTH SYSTEM

(71) Applicant: Marissa R. Lacayo, Sacramento, CA (US)

(72) Inventor: Marissa R. Lacayo, Sacramento, CA (US)

(*) Notice: Subject to any disclaimer, the term of this patent is extended or adjusted under 35 U.S.C. 154(b) by 633 days.

(21) Appl. No.: 13/890,484

(22) Filed: May 9, 2013

Related U.S. Application Data

(63) Continuation-in-part of application No. 12/711,472, filed on Feb. 24, 2010, now abandoned.

(60) Provisional application No. 61/209,130, filed on Mar. 4, 2009.

(51) Int. Cl.
| | | |
|---|---|---|
| A61M 37/00 | (2006.01) | |
| A61M 16/14 | (2006.01) | |
| A61H 33/06 | (2006.01) | |
| A61H 35/00 | (2006.01) | |

(52) U.S. Cl.
CPC ............ *A61M 16/14* (2013.01); *A61H 33/06* (2013.01); *A61H 2035/004* (2013.01); *A61H 2201/10* (2013.01)

(58) Field of Classification Search
CPC ............ F24F 11/0001; F24F 11/0012; F24F 11/053; F24F 2011/0002; F24F 2011/0006; G05D 23/19; G05D 23/1917; G05D 23/1927; G05D 23/193; G05D 23/1931; A61M 16/14; A61M 11/041; A61F 7/0053; A61H 33/06; A61H 33/065; A61H 33/067; A61H 2201/10; A61H 35/008; A61H 33/12
USPC .......................................... 4/524; 128/205.26
See application file for complete search history.

(56) References Cited

U.S. PATENT DOCUMENTS

| | | | | |
|---|---|---|---|---|
| 1,705,467 A | * | 3/1929 | Battenfeld | A61H 35/008 604/291 |
| 1,985,147 A | * | 12/1934 | Carlson | A47K 3/20 4/525 |
| 2,647,797 A | | 8/1953 | Moss | |
| 2,821,982 A | * | 2/1958 | Lyburn | A61H 33/06 4/531 |
| 3,564,201 A | | 2/1971 | Jones et al. | |
| 3,649,971 A | | 3/1972 | Basa | |
| 4,432,103 A | * | 2/1984 | Hunziker | A47K 3/284 4/525 |
| 4,699,136 A | | 10/1987 | Krauser | |
| 4,916,913 A | * | 4/1990 | Narikiyo | F24F 3/001 236/49.3 |
| 5,139,859 A | | 8/1992 | Karvanen | |
| 5,255,399 A | * | 10/1993 | Park | A61H 33/06 4/524 |
| 5,416,931 A | * | 5/1995 | Wolfenden | A61H 33/06 4/524 |
| 5,511,254 A | | 4/1996 | O'Brien | |
| 6,170,097 B1 | | 1/2001 | Lin | |
| 6,241,388 B1 | | 6/2001 | Terramani | |
| 6,745,411 B1 | * | 6/2004 | Kjonaas | A61H 33/063 4/524 |

(Continued)

*Primary Examiner* — Laura Bouchelle
*Assistant Examiner* — Morgan Lee

(57) ABSTRACT

A medicinal healing booth system for treating a user with medicated steam features a booth. A side panel of the booth features a transparent or translucent top panel section from a panel midpoint to a roof panel. A base panel of the booth features raised grating. The system features a door located in the side panel of the booth. The system features a control system and a steam generation system having a water tank with a heating element, a medicine tank, and a steam distribution nozzle. The medicine tank is fluidly connected to steam piping having the steam distribution nozzle located on a terminating end. The system features a temperature regulation system having an infrared light, a vent, and an automated vent valve. The system features a sterilization system having an ultraviolet light. A seat is located on the booth base panel.

1 Claim, 5 Drawing Sheets

(56) References Cited

U.S. PATENT DOCUMENTS

| | | |
|---|---|---|
| 6,904,624 B2 | 6/2005 | Leung et al. |
| 7,108,712 B2 | 9/2006 | Barghelame |
| 7,503,926 B2 | 3/2009 | Daffer et al. |
| 8,327,473 B2 | 12/2012 | Matsubara et al. |
| 2002/0190073 A1 | 12/2002 | Hewett |
| 2004/0030371 A1 | 2/2004 | Barghelame |
| 2005/0241058 A1 | 11/2005 | Li |
| 2006/0195979 A1 | 9/2006 | Liu |
| 2006/0229691 A1* | 10/2006 | Noskov ............... A61F 7/0053 607/96 |
| 2007/0113333 A1 | 5/2007 | Rivas |
| 2008/0004677 A1 | 1/2008 | Gay |
| 2008/0223788 A1 | 9/2008 | Rimdzius et al. |
| 2009/0070926 A1 | 3/2009 | Kjonaas |
| 2010/0017953 A1* | 1/2010 | O'Keeffe ............... A61H 33/06 4/524 |
| 2010/0289236 A1* | 11/2010 | Bennett .................... B62B 3/10 280/79.11 |
| 2012/0233764 A1* | 9/2012 | Lee ....................... A61H 33/06 4/524 |
| 2012/0233765 A1* | 9/2012 | Altman ............... A61H 33/005 4/524 |
| 2013/0025302 A1 | 1/2013 | Lyubchenko |

\* cited by examiner

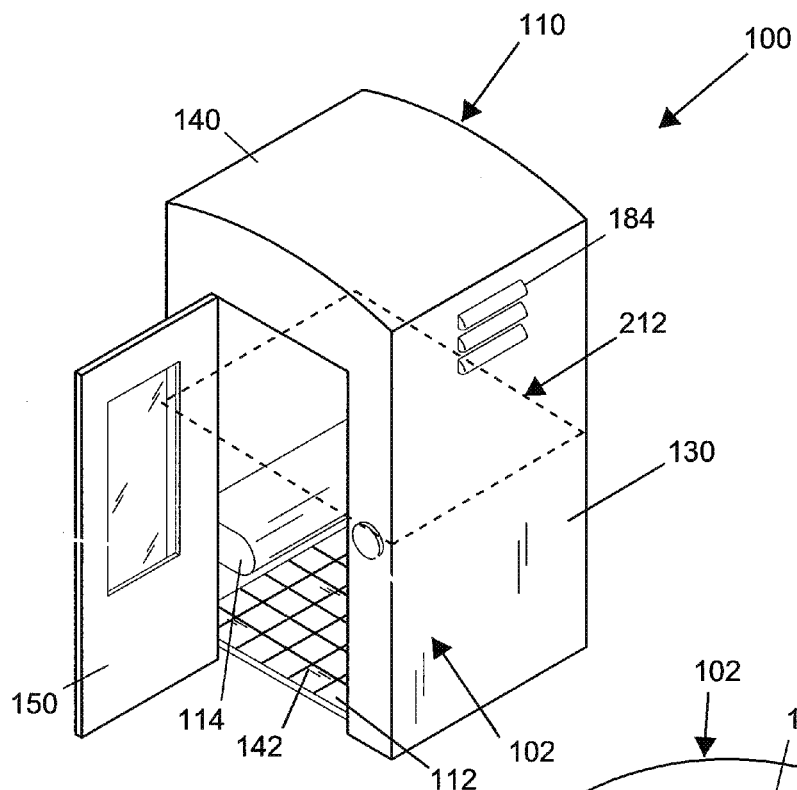
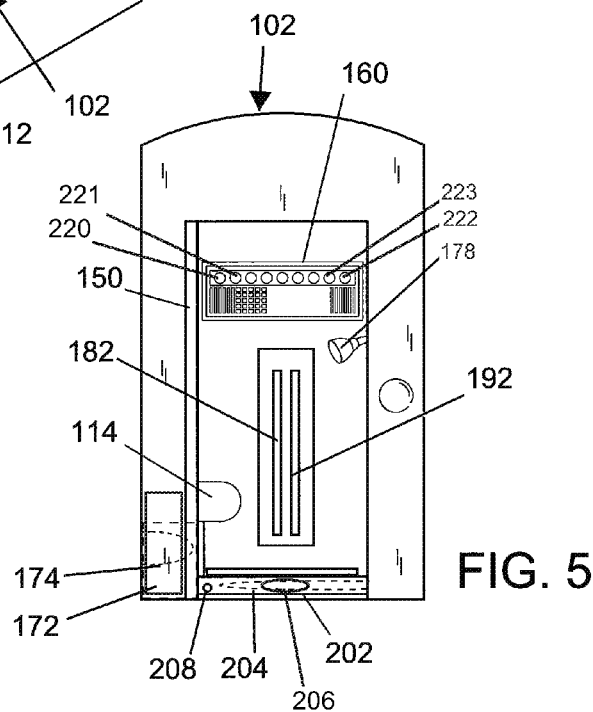

MEDICINAL HEALING BOOTH SYSTEM

CROSS REFERENCE

This application claims priority to U.S. patent application Ser. No. 12/711,472, filed Feb. 24, 2010, which is a non-provisional of U.S. Provisional Application No. 61/209,130 filed Mar. 4, 2009, the specification(s) of which is/are incorporated herein in their entirety by reference.

FIELD OF THE INVENTION

The present invention relates to a sauna-like system, or more particularly to medicinal healing booth system for treating a user with medicated steam.

BACKGROUND OF THE INVENTION

Many individuals suffer from ailments such as colds, allergies, asthma, and the like. Oftentimes individuals take over-the-counter medications or prescription medications to help ease the symptoms of such conditions and ailments. These medications, however, can often take a long time to make the individual feel better and may have harmful side effects. The present invention features a medicinal healing booth system for treating a user with medicated steam for helping to relieve symptoms of colds, allergies, and asthma. For example, the system can release medicated steam onto an individual within the booth and subject him/her to infrared light (e.g., 5-6 minutes). The medicinal healing booth system can also provide a quick and easy means of dispensing medication under medical supervision in hospitals, clinics, or the like, for example the medication may be released with the steam or vapor.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a medicinal healing booth system for treating a user with medicated steam. In some embodiments, the system comprises a booth. In some embodiments, a side panel comprises a transparent or translucent top panel section from a panel midpoint to the roof panel. In some embodiments, a base panel comprises raised grating. In some embodiments, the system comprises a door sealably located in the side panel of the booth.

In some embodiments, the system comprises a control system. In some embodiments, the system comprises a steam generation system having a water tank with a heating element, a medicine tank, and a steam distribution nozzle. In some embodiments, the medicine tank is fluidly connected to steam piping having the steam distribution nozzle located on a terminating end. In some embodiments, the system comprises a temperature regulation system having an infrared light, a vent, and an automated vent valve. In some embodiments, the system comprises a sterilization system having an ultraviolet light. In some embodiments, the system comprises a seat located on the booth base panel.

The disclosures of the following U.S. patents are incorporated in their entirety by reference herein: U.S. Pat. No. 7,503,926; U.S. Pat. No. 7,108,712; U.S. Pat. No. 6,904,624; U.S. Pat. No. 6,241,388; U.S. Pat. No. 6,170,097; U.S. Pat. No. 5,511,254; U.S. Pat. No. 5,139,859; U.S. Pat. No. 4,699,136; U.S. Pat. No. 3,649,971; U.S. Pat. No. 2,647,797 A; Patent Pub. No. 2002/0190073 A1; U.S. Patent Pub. No. 2004/0030371; U.S. Patent Pub. No. 2005/0241058 A1; U.S. Patent Pub. No. 2006/0195979; U.S. Patent Pub. No. 2007/0113333; U.S. Patent Pub. No. 2008/0004677 A1; U.S. Patent Pub. No. 008/022378 A1; and U.S. Patent Pub. No. 2009/0070926 A1.

BRIEF DESCRIPTION OF THE DRAWINGS

FIG. 4 shows a perspective view of the booth of the present invention.

FIG. 5 shows a front view of the booth of the present invention.

DESCRIPTION OF PREFERRED EMBODIMENTS

Figure 1:
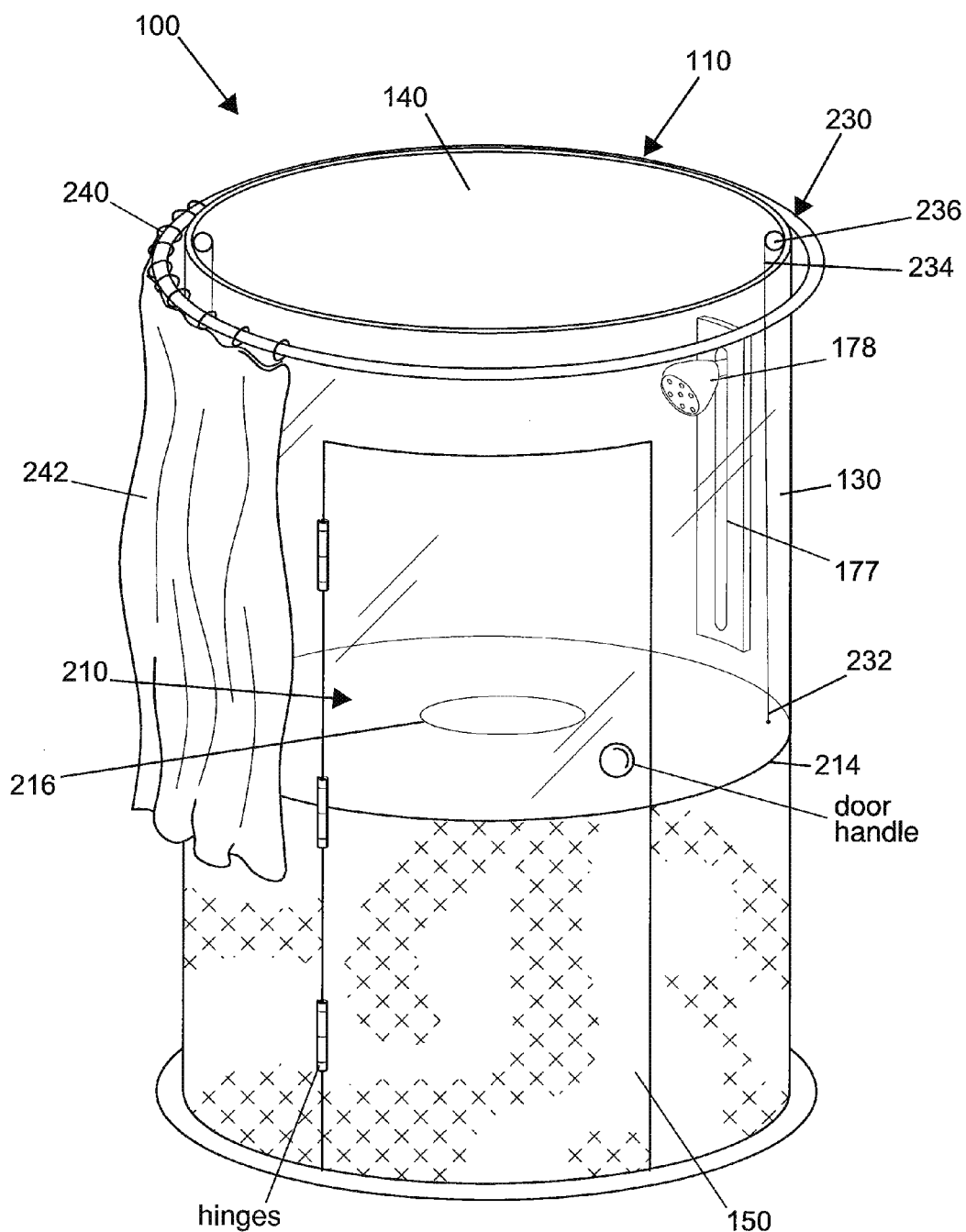
FIG. 1 shows a perspective view of the booth of the present invention.
Figure 2:
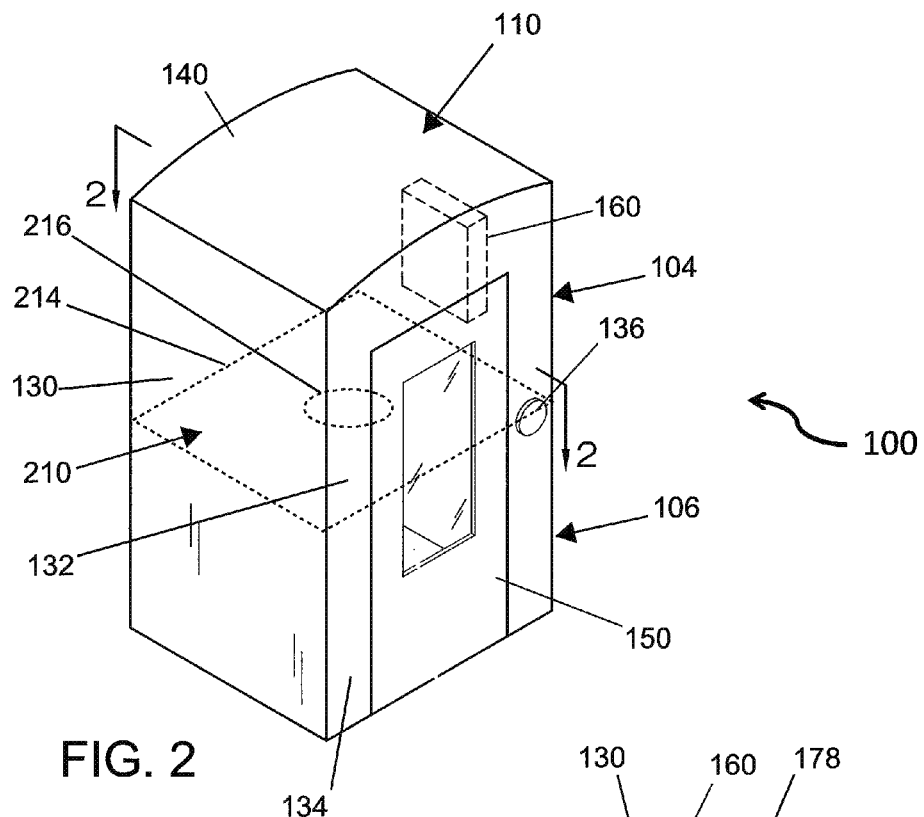
FIG. 2 shows a perspective view of the booth of the present invention.
Figure 3:
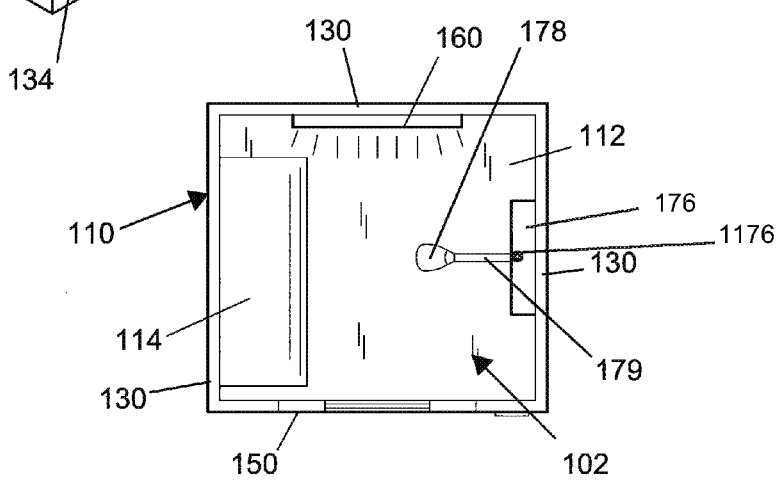
FIG. 3 shows a cross-sectional view of the booth of the present invention.
Figure 6:
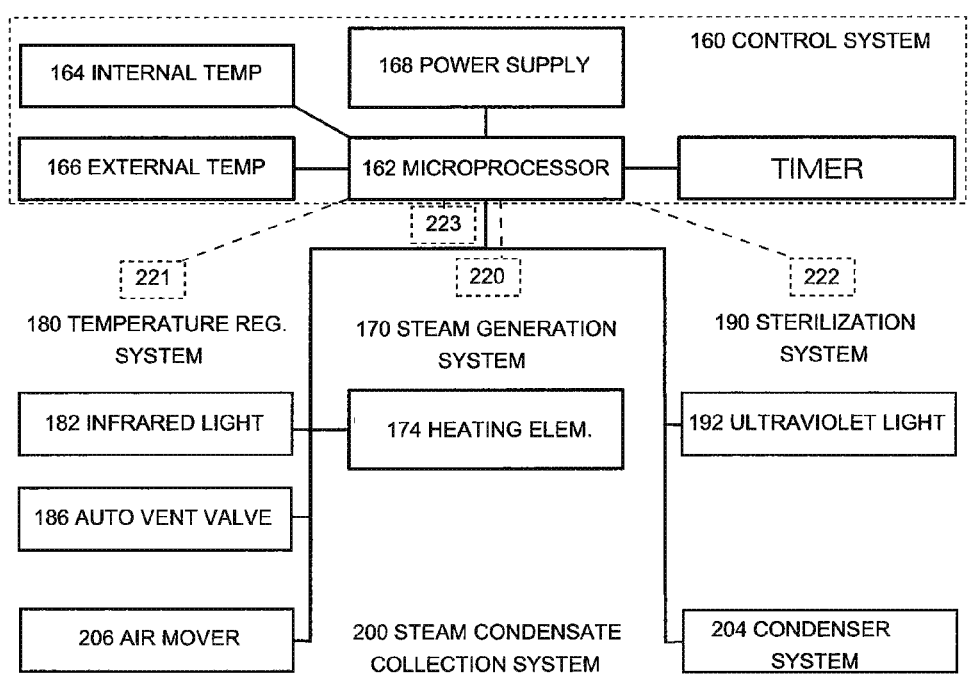
FIG. 6 shows a schematic view of the present invention.
Figure 7:
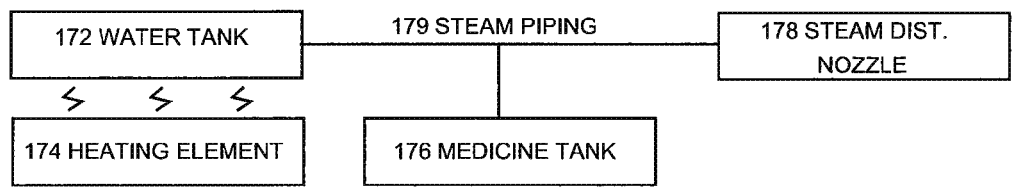
FIG. 7 shows a schematic view of the steam piping of the present invention.
Figure 8:
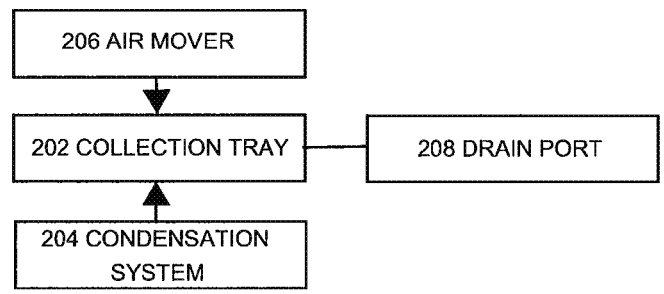
FIG. 8 shows a schematic view of the collection tray of the present invention.
Figure 9:
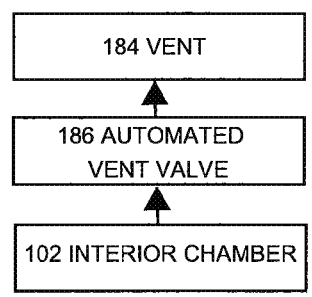
FIG. 9 shows a schematic view of the vent and the automated vent valve of the present invention.

Following is a list of elements corresponding to a particular element referred to herein:
100 Medicinal healing booth system
110 Booth
102 Interior chamber
104 Upper zone
106 Lower zone
112 Base panel
114 Seat
130 Side panel
132 Top panel section
134 Bottom panel section
136 Panel midpoint
140 Roof panel
142 Raised grating
150 Door
160 Control system
162 Microprocessor
164 Internal temperature sensor
166 External temperature sensor
168 Power supply
170 Steam generation system
172 Water tank
174 Heating element
176 Medicine tank
177 Adjustable track
178 Steam distribution nozzle
179 Steam piping
180 Temperature regulation system
182 Infrared light
184 Vent
186 Automated vent valve
190 Sterilization system 192 Ultraviolet light
200 Steam condensation collection system
202 Collection tray
204 Condenser system
206 Air mover
208 Drain port
210 Isolation collar
212 Plane
214 Isolation collar edge
216 Neck aperture
220 First control switch
221 Second control switch
222 Third control switch
223 Fourth control switch
230 Retraction system
232 Retractor first end
234 Retractor second end
236 Retractor brake Referring now to FIG. 1-9, the present invention features a medicinal healing booth system (100) for treating a user with medicated steam. In some embodiments, the steam is medicated with pharmaceuticals. In some embodiments, the steam is medicated with herbs. In some embodiments, the system (100) comprises a booth (110) having a base panel (112), a side panel (130), and a roof panel (140). In some embodiments, the booth (110) comprises two side panels (130). In some embodiments, the booth (110) comprises three side panels (130). In some embodiments, the booth (110) comprises four side panels (130). In some embodiments, the booth (110) comprises more than four side panels (130).

In some embodiments, the side panel (130) comprises a top panel section (132) from a panel midpoint (136) to the roof panel (140) and a bottom panel section (134) from the panel midpoint (136) to the base panel (112). In some embodiments, the top panel section (132) is transparent or translucent. In some embodiments, the roof panel (140) is transparent or translucent. In some embodiments, the top panel section (132) and/or the roof panel (140) is constructed from decorative material. In some embodiments, the base panel (112) comprises raised grating (142) located thereon for a user to stand upon.

In some embodiments, the system (100) comprises a door (150) sealably located in the side panel (130) of the booth (110). In some embodiments, the door (150) has a window. In some embodiments, the door (150) is a regular door (150) well known to those of ordinary skill in the art.

In some embodiments, the system (100) comprises a control system (160) having a microprocessor (162), an internal temperature sensor (164), and an external temperature sensor (166). In some embodiments, the internal temperature sensor (164) and the external temperature sensor (166) are operatively connected to the microprocessor (162). In some embodiments, the microprocessor (162) is operatively connected to a power supply (168).

In some embodiments, the system (100) comprises a steam generation system (170) having a water tank (172) with a heating element (174) located therein, a medicine tank (176), and a steam distribution nozzle (178). In some embodiments, the steam distribution nozzle (178) is located on a vertically adjustable track (177). In some embodiments, the steam distribution nozzle (178) is vertically adjustable in order to position the steam distribution nozzle (178) near the face of the user. In some embodiments, the vertically adjustable track (177) is located on the side panel (130) and holds the steam distribution nozzle (178) via a position securing means. In some embodiments, steam piping (179) is flexible to accommodate adjustment of the vertically adjustable track (177). In some embodiments, the water tank (172) is fluidly connected to a water supply. In some embodiments, the heating element (174) is operatively connected to the power supply (168) and the microprocessor (162). In some embodiments, the medicine tank (176) is fluidly connected to steam piping (179) having the steam distribution nozzle (178) located on a terminating end thereon. In some embodiments, the medicine tank (176) comprises a metering orifice or a valve (1176) located thereon for ensuring proportionate flow into the steam piping (179). In some embodiments, the steam generation system (170) comprises a first control switch (220) located on the booth (110). In some embodiments, the first control switch (220) is operatively connected to the microprocessor (162). In some embodiments, the first control switch (220) is configured to activate and deactivate the steam generation system (170).

In some embodiments, the system (100) comprises a temperature regulation system (180) having an infrared light (182), a vent (184), and an automated vent valve (186). In some embodiments, the infrared light (182) is located in the side panel (130) thereon and operatively connected to the power supply (168) and the microprocessor (162). In some embodiments, the vent (184) is fluidly connected to a booth interior chamber (102). In some embodiments, the automated vent valve (186) is located between the vent (184) and the interior chamber (102) and operatively connected to the power supply (168) and the microprocessor (162). In some embodiments, the automated vent valve (186) is a baffle. In some embodiments, the temperature regulation system (180) comprises a second control switch (221) located on the booth (110). In some embodiments, the second control switch (221) is operatively connected to the microprocessor (162). In some embodiments, the second control switch (221) is configured to activate and deactivate the temperature regulation system (180).

In some embodiments, the system (100) comprises a sterilization system (190) having an ultraviolet light (192). In some embodiments, the ultraviolet light (192) is located in the side panel (130) thereon and operatively connected to the power supply (168) and the microprocessor (162). In some embodiments, the sterilization system (190) comprises two ultraviolet lights (192). In some embodiments, the sterilization system (190) comprises three or more ultraviolet lights (192). In some embodiments, the sterilization system (190) comprises a third control switch (222) located on the booth (110). In some embodiments, the third control switch (222) is operatively connected to the microprocessor (162). In some embodiments, the third control switch (222) is configured to activate and deactivate the sterilization system (190).

In some embodiments, the system (100) comprises a seat (114) located on the booth base panel (112). In some embodiments, the seat (114) is integrated with a water tank (172).

In some embodiments, for operation a user is located in the booth (110) with the door (150) in a closed position. In some embodiments, upon activation of the first control switch (220), the microprocessor (162) is configured to send a first signal to the heating element (174) to generate steam from water in the water tank (172) via the heating element (174). In some embodiments, a medicinal composition is introduced to and vaporized by the steam traversing the steam piping (179) via a metering device located on the medicine tank (176). In some embodiments, a vaporous mixture of steam and the medicinal composition exits the steam distribution nozzle (178) positioned close to a face of the user for inhalation. In some embodiments, upon deactivation of the first control switch (220), the steam generation system (170) is deactivated.

In some embodiments, upon activation of the second control switch (221), the microprocessor (162) is configured to send a second signal to energize the infrared light (182) to heat the booth (110) via the infrared light (182). In some embodiments, for control, the microprocessor (162) is configured to compare the internal temperature with the external temperature. In some embodiments, the external temperature sensor (166) sends a fourth signal to the microprocessor (162) and the internal temperature sensor (164) sends a fifth signal to the microprocessor (162). In some embodiments, the microprocessor (162) is configured to control an internal temperature via heat from the infrared light (182) and releasing heat from the automated vent valve (186) through the vent (184). In some embodiments, if the internal temperature sensor (164) detects a temperature exceeding a temperature limit, the automated vent valve (186) is activated for releasing the vaporous mixture of steam and the medicinal composition outside the booth (110) via the vent (184) to an ambient temperature air environment while simultaneously allowing replacement ambient temperature air inside.

In some embodiments, upon deactivation of the second control switch (221), the microprocessor (162) is configured to send a third signal to the automated vent valve (186) to release the vaporous mixture of steam and the medicinal composition from the booth (110) via the vent (184) until the internal temperature as measured by the internal temperature sensor (164) reaches the external temperature as measured by the external temperature sensor (166). In some embodiments, when the internal temperature equals the external temperature, an indicator alerts the user.

In some embodiments, for sterilization, the microprocessor (162) sends a sixth signal to the ultraviolet light (192) for sterilization via exposing the booth (110) to the ultraviolet light (192).

In some embodiments, the booth (110) comprises a steam condensation collection system (200) located on the base panel (112) beneath the raised grating (142). In some embodiments, the steam condensation collection system (200) comprises a collection tray (202), a condenser system (204) located in the collection tray (202), an air mover (206), and a drain port (208). In some embodiments, the condenser system (204) is operatively connected to the microprocessor (162) and the power supply (168). In some embodiments, the air mover (206) is operatively connected to the microprocessor (162) and the power supply (168). In some embodiments, the microprocessor (162) is configured to operate the condenser system (204) and the air mover (206). In some embodiments, the vaporous mixture of steam and the medicinal composition is drawn to the condenser system (204) via the air mover (206). In some embodiments, the vaporous mixture of steam and the medicinal composition is condensed and collected via the collection tray (202). In some embodiments, the vaporous mixture of steam and the medicinal composition is drained via the drain port (208).

In some embodiments, the booth (110) comprises an isolation collar (210) having a planar surface. In some embodiments, the isolation collar (120) is transparent or translucent. In some embodiments, an isolation collar edge (214) is sealably located on a close side panel (130) via a seal. In some embodiments, the isolation collar (210) is slidably located on the close side panel (130). In some embodiments, the isolation collar (210) comprises a neck aperture (216) centrally located therein. In some embodiments, the neck aperture (216) sealably interfaces with a neck of the user. In some embodiments, the isolation collar (210) is designed to isolate the booth (110) into an upper zone (104) for treating a user with the vaporous mixture of steam and the medicinal composition via inhalation and a lower zone (106) for keeping the user dry from the neck downward and unexposed to the vaporous mixture of steam and the medicinal composition.

In some embodiments, the isolation collar (210) is located on a spring-biased retraction system (230) for holding an elevation based on a height of the user. In some embodiments, a retractor first end (232) is located on the isolation collar (210). In some embodiments, a retractor second end (234) is located at the roof panel (140). In some embodiments, the retraction system (230) is spring-biased to apply a force to draw the isolation collar (210) toward the roof panel (140). In some embodiments, the user can pull down on the isolation collar (210) to a desired height and apply a retractor brake (236) to hold the isolation collar (210) temporarily in position for use. In some embodiments, upon release, the isolation collar (210) is controllably drawn toward the roof panel (140).

In some embodiments, the isolation collar (210) is rigid. In some embodiments, the isolation collar (210) is pliable.

In some embodiments, the isolation collar (210) is suspended on a spring biased cable system to adapt to a height of a user. In some embodiments, the isolation collar (210) slides up and down inside the booth (110) to adjust. In some embodiments, the isolation collar (210) adjustment is motorized having a motor attached to the roof panel (140), a spool on the motor, and a winding cable wound around the spool and attached to the isolation collar (210). In some embodiments, the isolation collar (210) is held in a static position with counter spring attached to the isolation collar (210).

In some embodiments, the isolation collar (210) lies on a plane (212) perpendicular to the side panel (130) at the panel midpoint (136).

In some embodiments, a curtain rod (240) having a curtain (242) slidably located thereon is located on the booth side panel (130) of a booth exterior close to the roof panel (140) for covering the booth (110).

In some embodiments, the steam generation system (170), the temperature regulation system (180), and the sterilization system (190) are controlled by a timed cycle. In some embodiments, the microprocessor (162) is configured to control the steam generation system (170), the temperature regulation system (180), and the sterilization system (190).

In some embodiments, a fourth control switch (223) is located in a lower zone (106). In some embodiments, the fourth control switch (223) is operatively connected to the microprocessor (162). In some embodiments, the fourth control switch (223) is a shut-off switch (or an emergency shut-off switch) for the steam generation system (170), the temperature regulation system (180), and the sterilization system (190) for the user.

In some embodiments, a medicinal healing booth system (100) for treating a user with medicated steam consists of a booth (110) having a base panel (112), a side panel (130), and a roof panel (140). In some embodiments, the side panel (130) consists of a top panel section (132) from a panel midpoint (136) to the roof panel (140) and a bottom panel section (134) from the panel midpoint (136) to the base panel (112). In some embodiments, the top panel section (132) is transparent or translucent. In some embodiments, the roof panel (140) is transparent or translucent. In some embodiments, the base panel (112) consists of raised grating (142) located thereon for a user to stand upon.

In some embodiments, the system (100) consists of a door (150) sealably located in the side panel (130) of the booth (110).

In some embodiments, the system (100) consists of a control system (160) having a microprocessor (162), an internal temperature sensor (164), and an external temperature sensor (166). In some embodiments, the internal temperature sensor (164) and the external temperature sensor (166) are operatively connected to the microprocessor (162). In some embodiments, the microprocessor (162) is operatively connected to a power supply (168).

In some embodiments, the system (100) consists of a steam generation system (170) having a water tank (172) with a heating element (174) located therein, a medicine tank (176), and a steam distribution nozzle (178). In some embodiments, the water tank (172) is fluidly connected to a water supply. In some embodiments, the heating element (174) is operatively connected to the power supply (168) and the microprocessor (162). In some embodiments, the medicine tank (176) is fluidly connected to steam piping (179) having the steam distribution nozzle (178) located on a terminating end thereon. In some embodiments, the steam generation system (170) consists of a first control switch (220) located on the booth (110). In some embodiments, the first control switch (220) is operatively connected to the microprocessor (162). In some embodiments, the first control switch (220) is configured to activate and deactivate the steam generation system (170).

In some embodiments, the system (100) consists of a temperature regulation system (180) having an infrared light (182), a vent (184), and an automated vent valve (186). In some embodiments, the infrared light (182) is located in the side panel (130) thereon and operatively connected to the power supply (168) and the microprocessor (162). In some embodiments, the vent (184) is fluidly connected to a booth interior chamber (102). In some embodiments, the automated vent valve (186) is located between the vent (184) and the interior chamber (102) and operatively connected to the power supply (168) and the microprocessor (162). In some embodiments, the temperature regulation system (180) consists of a second control switch (221) located on the booth (110). In some embodiments, the second control switch (221) is operatively connected to the microprocessor (162). In some embodiments, the second control switch (221) is configured to activate and deactivate the temperature regulation system (180).

In some embodiments, the system (100) consists of a sterilization system (190) having an ultraviolet light (192). In some embodiments, the ultraviolet light (192) is located in the side panel (130) thereon and operatively connected to the power supply (168) and the microprocessor (162). In some embodiments, the sterilization system (190) consists of a third control switch (222) located on the booth (110). In some embodiments, the third control switch (222) is operatively connected to the microprocessor (162). In some embodiments, the third control switch (222) is configured to activate and deactivate the sterilization system (190).

In some embodiments, the system (100) consists of a seat (114) located on the booth base panel (112).

In some embodiments, the system (100) consists of a steam condensation collection system (200) located on the base panel (112) beneath the raised grating (142). In some embodiments, the steam condensation collection system (200) consists of a collection tray (202), a condenser system (204) located in the collection tray (202), an air mover (206), and a drain port (208). In some embodiments, the condenser system (204) is operatively connected to the microprocessor (162) and the power supply (168). In some embodiments, the air mover (206) is operatively connected to the microprocessor (162) and the power supply (168). In some embodiments, the microprocessor (162) is configured to operate the condenser system (204) and the air mover (206). In some embodiments, the vaporous mixture of steam and the medicinal composition is drawn to the condenser system (204) via the air mover (206). In some embodiments, the vaporous mixture of steam and the medicinal composition is condensed and collected via the collection tray (202). In some embodiments, the vaporous mixture of steam and the medicinal composition is drained via the drain port (208).

In some embodiments, the system (100) consists of an isolation collar (210) having a planar surface. In some embodiments, an isolation collar edge (214) is sealably located on a close side panel (130) via a seal. In some embodiments, the isolation collar (210) is slidably located on the close side panel (130). In some embodiments, the isolation collar (210) consists of a neck aperture (216) centrally located therein. In some embodiments, the neck aperture (216) sealably interfaces with a neck of the user. In some embodiments, the isolation collar (210) is designed to isolate the booth (110) into an upper zone (104) for treating a user with the vaporous mixture of steam and the medicinal composition via inhalation and a lower zone (106) for keeping the user dry from the neck downward and unexposed to the vaporous mixture of steam and the medicinal composition. In some embodiments, the isolation collar (210) lies on a plane (212) perpendicular to the side panel (130) at the panel midpoint (136).

In some embodiments, the system (100) consists of a curtain rod (240) having a curtain (242) slidably located thereon located on the booth side panel (130) of a booth exterior close to the roof panel (140).

In some embodiments, the system (100) consists of a fourth control switch (223) located in a lower zone (106). In some embodiments, the fourth control switch (223) is operatively connected to the microprocessor (162). In some embodiments, the fourth control switch (223) is a shut-off switch for the steam generation system (170). In some embodiments, the temperature regulation system (180), and the sterilization system (190) for the user.

In some embodiments, for operation a user is located in the booth (110) with the door (150) in a closed position. In some embodiments, upon activation of the first control switch (220), the microprocessor (162) is configured to send a first signal to the heating element (174) to generate steam from water in the water tank (172) via the heating element (174). In some embodiments, a medicinal composition is introduced to and vaporized by the steam traversing the steam piping (179) via a metering device located on the medicine tank (176). In some embodiments, a vaporous mixture of steam and the medicinal composition exits the steam distribution nozzle (178) positioned close to a face of the user for inhalation. In some embodiments, upon deactivation of the first control switch (220), the steam generation system (170) is deactivated.

In some embodiments, upon activation of the second control switch (221), the microprocessor (162) is configured to send a second signal to energize the infrared light (182) to heat the booth (110) via the infrared light (182). In some embodiments, for control, the microprocessor (162) is configured to compare the internal temperature with the external temperature. In some embodiments, the external temperature sensor (166) sends a fourth signal to the microprocessor (162) and the internal temperature sensor (164) sends a fifth signal to the microprocessor (162). In some embodiments, the microprocessor (162) is configured to control an internal temperature via heat from the infrared light (182) and releasing heat from the automated vent valve (186) through the vent (184). In some embodiments, if the internal temperature sensor (164) detects a temperature exceeding a temperature limit, the automated vent valve (186) is activated for releasing the vaporous mixture of steam and the medicinal composition outside the booth (110) via the vent (184) to an ambient temperature air environment while simultaneously allowing replacement ambient temperature air inside.

In some embodiments, upon deactivation of the second control switch (221), the microprocessor (162) is configured to send a third signal to the automated vent valve (186) to release the vaporous mixture of steam and the medicinal composition from the booth (110) via the vent (184) until the internal temperature as measured by the internal temperature sensor (164) reaches the external temperature as measured by the external temperature sensor (166). In some embodiments, when the internal temperature equals the external temperature, an indicator alerts the user.

In some embodiments, for sterilization, the microprocessor (162) sends a sixth signal to the ultraviolet light (192) for sterilization via exposing the booth (110) to the ultraviolet light (192).

In some embodiments, the steam generation system (170), the temperature regulation system (180), and the sterilization system (190) are controlled by a timed cycle. In some embodiments, the microprocessor (162) is configured to control the steam generation system (170), the temperature regulation system (180), and the sterilization system (190).

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A medicinal healing booth system (100) for treating a user with medicated steam, wherein the system (100) consists of:

(a) a booth (110) having a base panel (112), a side panel (130), and a roof panel (140), wherein the side panel (130) consists of a top panel section (132) from a panel midpoint (136) to the roof panel (140) and a bottom panel section (134) from the panel midpoint (136) to the base panel (112), wherein the top panel section (132) is transparent or translucent, wherein the roof panel (140) is transparent or translucent, wherein the base panel (112) consists of raised grating (142) disposed thereon for a user to stand upon;

(b) a door (150) sealably disposed in the side panel (130) of the booth (110);

(c) a control system (160) having a microprocessor (162), an internal temperature sensor (164), and an external temperature sensor (166), wherein the internal temperature sensor (164) and the external temperature sensor (166) are operatively connected to the microprocessor (162), wherein the microprocessor (162) is operatively connected to a power supply (168);

(d) a steam generation system (170) having a water tank (172) with a heating element (174) disposed therein, a medicine tank (176), and a steam distribution nozzle (178) disposed on a vertically adjustable track (177), wherein the water tank (172) is fluidly connected to a water supply, wherein the heating element (174) is operatively connected to the power supply (168) and the microprocessor (162), wherein the medicine tank (176) is fluidly connected to steam piping (179) having the steam distribution nozzle (178) disposed on a terminating end thereon, wherein the steam generation system (170) consists of a first control switch (220) disposed on the booth (110), wherein the first control switch (220) is operatively connected to the microprocessor (162), wherein the first control switch (220) is configured to activate and deactivate the steam generation system (170);

(e) a temperature regulation system (180) having an infrared light (182), a vent (184), and an automated vent valve (186), wherein the infrared light (182) is disposed in the side panel (130) thereon and operatively connected to the power supply (168) and the microprocessor (162), wherein the vent (184) is fluidly connected to a booth interior chamber (102), wherein the automated vent valve (186) is disposed between the vent (184) and the interior chamber (102) and operatively connected to the power supply (168) and the microprocessor (162), wherein the temperature regulation system (180) consists of a second control switch (221) disposed on the booth (110), wherein the second control switch (221) is operatively connected to the microprocessor (162), wherein the second control switch (221) is configured to activate and deactivate the temperature regulation system (180);

(f) a sterilization system (190) having an ultraviolet light (192), wherein the ultraviolet light (192) is disposed in the side panel (130) thereon and operatively connected to the power supply (168) and the microprocessor (162), wherein the sterilization system (190) consists of a third control switch (222) disposed on the booth (110), wherein the third control switch (222) is operatively connected to the microprocessor (162), wherein the third control switch (222) is configured to activate and deactivate the sterilization system (190);

(g) a seat (114) disposed on the booth base panel (112);

(h) a steam condensation collection system (200) disposed on the base panel (112) beneath the raised grating (142), wherein the steam condensation collection system (200) consists of a collection tray (202), a condenser system (204) disposed in the collection tray (202), an air mover (206), and a drain port (208), wherein the condenser system (204) is operatively connected to the microprocessor (162) and the power supply (168), wherein the air mover (206) is operatively connected to the microprocessor (162) and the power supply (168), wherein the microprocessor (162) is configured to operate the condenser system (204) and the air mover (206), wherein the vaporous mixture of steam and the medicinal composition is drawn to the condenser system (204) via the air mover (206), wherein the vaporous mixture of steam and the medicinal composition is condensed and collected via the collection tray (202), wherein the vaporous mixture of steam and the medicinal composition is drained via the drain port (208);

(i) an isolation collar (210) having a planar surface, wherein an isolation collar edge (214) is sealably disposed on a proximal side panel (130) via a seal, wherein the isolation collar (210) is slidably disposed on the proximal side panel (130), wherein the isolation collar (210) consists of a neck aperture (216) centrally disposed therein, wherein the neck aperture (216) is configured to sealably interface with a neck of the user, wherein the isolation collar (210) is designed to isolate the booth (110) into an upper zone (104) for treating a user with the vaporous mixture of steam and the medicinal composition via inhalation and a lower zone (106) for keeping the user dry from the neck downward and unexposed to the vaporous mixture of steam and the medicinal composition, wherein the isolation collar (210) lies on a plane (212) perpendicular to the side panel (130) at the panel midpoint (136), wherein the isolation collar (210) is disposed on a spring-biased retraction system (230) for holding an elevation based on a height of the user, wherein a retractor first end (232) is disposed on the isolation collar (210), wherein a retractor second end (234) is disposed at the roof panel (140), wherein the retraction system (230) is spring-biased to apply a force to draw the isolation collar (210) toward the roof panel (140), wherein the user can pull down on the isolation collar (210) to a desired height and apply a retractor brake (236) to hold the isolation collar (210) temporarily in position for use, wherein upon release, the isolation collar (210) is controllably drawn toward the roof panel (140);

(j) a curtain rod (240) having a curtain (242) slidably disposed thereon is disposed on the booth side panel (130) of a booth exterior proximal to the roof panel (140); and (k) a fourth control switch (223) is disposed in a lower zone (106), wherein the fourth control switch (223) is operatively connected to the microprocessor (162), wherein the fourth control switch (223) is a shut-off switch for the steam generation system (170), the temperature regulation system (180), and the sterilization system (190) for the user;

wherein for operation a user is disposed in the booth (110) with the door (150) in a closed position, wherein upon activation of the first control switch (220), the microprocessor (162) is configured to send a first signal to the heating element (174) to generate steam from water in the water tank (172) via the heating element (174), wherein a medicinal composition is introduced to and vaporized by the steam traversing the steam piping (179) via a metering device disposed on the medicine tank (176), wherein a vaporous mixture of steam and the medicinal composition exits the steam distribution nozzle (178) positioned proximal to a face of the user for inhalation, wherein upon deactivation of the first control switch (220), the steam generation system (170) is deactivated;

wherein upon activation of the second control switch (221), the microprocessor (162) is configured to send a second signal to energize the infrared light (182) to heat the booth (110) via the infrared light (182), wherein for control, the microprocessor (162) is configured to compare an internal temperature with an external temperature, wherein the external temperature sensor (166) sends a fourth signal to the microprocessor (162) and the internal temperature sensor (164) sends a fifth signal to the microprocessor (162), wherein the microprocessor (162) is configured to control the internal temperature via heat from the infrared light (182) and releasing heat from the automated vent valve (186) through the vent (184), wherein if the internal temperature sensor (164) detects a temperature exceeding a temperature limit, the automated vent valve (186) is activated for releasing the vaporous mixture of steam and the medicinal composition outside the booth (110) via the vent (184) to an ambient temperature air environment while simultaneously allowing replacement ambient temperature air inside;

wherein upon deactivation of the second control switch (221), the microprocessor (162) is configured to send a third signal to the automated vent valve (186) to release the vaporous mixture of steam and the medicinal composition from the booth (110) via the vent (184) until the internal temperature as measured by the internal temperature sensor (164) reaches the external temperature as measured by the external temperature sensor (166), wherein when the internal temperature equals the external temperature, an indicator alerts the user;

wherein for sterilization, the microprocessor (162) sends a sixth signal to the ultraviolet light (192) for sterilization via exposing the booth (110) to the ultraviolet light (192);

wherein the steam generation system (170), the temperature regulation system (180), and the sterilization system (190) are controlled by a timed cycle, wherein the microprocessor (162) is configured to control the steam generation system (170), the temperature regulation system (180), and the sterilization system (190).

* * * * *